United States Patent
Holladay et al.

(10) Patent No.: US 7,615,652 B2
(45) Date of Patent: Nov. 10, 2009

(54) TWO-STAGE DEHYDRATION OF SUGARS

(75) Inventors: Johnathan E. Holladay, Kennewick, WA (US); Jianli Hu, Kennewick, WA (US); Yong Wang, Richland, WA (US); Todd A. Werpy, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 462 days.

(21) Appl. No.: 11/341,930

(22) Filed: Jan. 26, 2006

(65) Prior Publication Data

US 2007/0173651 A1 Jul. 26, 2007

(51) Int. Cl.
- C07C 29/00 (2006.01)
- C07D 315/00 (2006.01)
- C07D 493/00 (2006.01)
- C07H 1/00 (2006.01)
- C07H 17/00 (2006.01)
- C07H 5/04 (2006.01)
- C07H 1/06 (2006.01)
- C13K 5/00 (2006.01)

(52) U.S. Cl. .............. 549/464; 536/18.5; 536/18.6; 536/55.3; 536/123.13; 536/127; 536/18.7; 536/126; 536/124; 549/417; 568/902

(58) Field of Classification Search ........... 536/18.5, 536/18.6, 18.7, 55.3, 123.1, 123.13, 124, 536/126, 127; 549/417, 464; 568/902

See application file for complete search history.

(56) References Cited

U.S. PATENT DOCUMENTS

| | | | |
|---|---|---|---|
| 3,160,641 A | 12/1964 | Hartmann et al. | |
| 4,297,290 A | 10/1981 | Stockburger | |
| 4,408,061 A | 10/1983 | Salzburg et al. | |
| 4,506,086 A | 3/1985 | Salzburg et al. | |
| 4,564,692 A | 1/1986 | Feldmann et al. | |
| 4,861,513 A | 8/1989 | Lueders et al. | |
| 5,093,535 A | 3/1992 | Harrison et al. | |
| 6,013,812 A | 1/2000 | Haas et al. | |
| 6,124,443 A | 9/2000 | Darsow | |
| 6,392,062 B1 | 5/2002 | Haas | |
| 6,407,266 B2 | 6/2002 | Bhatia | |
| 6,639,067 B1 | 10/2003 | Brinegar et al. | |
| 6,689,892 B2 | 2/2004 | Andrews et al. | |
| 6,693,209 B2 | 2/2004 | Van Es et al. | |
| 7,439,352 B2 | 10/2008 | Moore et al. | |
| 2002/0052516 A1 | 5/2002 | Moore et al. | |
| 2003/0097028 A1 | 5/2003 | Fuertes | |
| 2003/0229235 A1 | 12/2003 | Bhatia | |
| 2004/0030161 A1 | 2/2004 | Bhatia | |
| 2004/0110969 A1 | 6/2004 | Fleche et al. | |
| 2004/0110994 A1 | 6/2004 | Bhatia | |

FOREIGN PATENT DOCUMENTS

| | | |
|---|---|---|
| CA | 1178288 | 11/1984 |
| EP | 0061055 A1 | 9/1982 |
| EP | 0201067 A2 | 11/1986 |
| EP | 0380402 A1 | 8/1990 |
| EP | 0915091 A2 | 5/1999 |
| EP | 1179535 A1 | 2/2002 |
| EP | 1179536 A1 | 2/2002 |
| WO | 9721697 A1 | 6/1997 |
| WO | 0014081 A1 | 3/2000 |
| WO | 0041985 | 7/2000 |
| WO | 0172136 A1 | 10/2001 |
| WO | 0194352 A1 | 12/2001 |
| WO | 0239957 A2 | 5/2002 |
| WO | 03022064 A1 | 3/2003 |
| WO | 03089436 A1 | 10/2003 |
| WO | 03089445 A1 | 10/2003 |
| WO | 2005047228 A1 | 5/2005 |

OTHER PUBLICATIONS

Fleche, et al., "Isosorbide" Starch/Starke, vol. 38, 1986, pp. 26-30.
2006 Chemical Abstracts Catalog, published 2006 by Chemical Abstracts Service. p. 52.

Primary Examiner—Taylor Victor Oh
(74) Attorney, Agent, or Firm—Wells St. Lohn P.S.

(57) ABSTRACT

The invention includes methods for producing dianhydrosugar alcohol by providing an acid catalyst within a reactor and passing a starting material through the reactor at a first temperature. At least a portion of the staring material is converted to a monoanhydrosugar isomer during the passing through the column. The monoanhydrosugar is subjected to a second temperature which is greater than the first to produce a dianhydrosugar. The invention includes a method of producing isosorbide. An initial feed stream containing sorbitol is fed into a continuous reactor containing an acid catalyst at a temperature of less than 120° C. The residence time for the reactor is less than or equal to about 30 minutes. Sorbitol converted to 1,4-sorbitan in the continuous reactor is subsequently provided to a second reactor and is dehydrated at a temperature of at least 120° C. to produce isosorbide.

18 Claims, No Drawings

TWO-STAGE DEHYDRATION OF SUGARS

CONTRACTUAL ORIGIN OF THE INVENTION

This invention was made with Government support under contract DE-AC0676RLO-1830, awarded by the U.S. Department of Energy. The Government has certain rights in this invention.

TECHNICAL FIELD

The invention pertains to methods for producing dianhydrosugar alcohols and methods of producing isosorbide.

BACKGROUND OF THE INVENTION

Isosorbide and various other dianhydrosugars are commercially valuable for a variety of applications such as use as copolymers for improving properties of polymer materials, for use as therapeutic agents, emulsifiers or as biodegradable surfactants. Conventional dehydration of sugars typically produces multiple anhydrosugars and/or dianhydrosugars products, and can also result in formation of various byproducts. During the production of dianhydrosugars, the generation of multiple monoanhydrosugar intermediates can result in low selectivity with respect to the desired dianhydrosugar product. Conventional sugar dehydration processes can typically produce significant amounts of undesired monoanhydrosugars as intermediates which limits selective production and yield of the desired dianhydrosugar.

It is desirable to develop alternative methods for dianhydrosugar production.

SUMMARY OF THE INVENTION

In one aspect, the invention encompasses methods for producing dianhydrosugar alcohol. The method includes providing a solid and/or soluble acid catalyst within a continuous reactor and passing a starting material through the reactor at a first temperature within the range of from about 70° C. to about 140° C. The starting material contains an initial compound, at least a portion of which is converted to a monoanhydrosugar isomer during the passing through the column. The residence time within the column is from about 10 minutes to about 30 minutes. A product material is obtained from the continuous reactor and contains a monoanhydrosugar isomer at an abundance of at least 50% relative to total monoanhydrosugars in the product material. The monoanhydrosugar isomer is subjected to a second temperature to convert at least some of the monoanhydrosugar isomer to a dianhydrosugar alcohol with the second temperature being greater than the first temperature.

In one aspect, the invention encompasses a method of producing isosorbide. An initial feed stream containing sorbitol is fed into a continuous reactor. The sorbitol in the feed stream is exposed to an acid catalyst within the continuous reactor, where the exposing is conducted at a temperature of less than 120° C. The residence time for the reactor is less than or equal to about 30 minutes. At least some of the sorbitol is converted to 1,4-sorbitan during the exposing and the 1,4-sorbitan is subsequently provided in a second feed stream to a second reactor. The sorbitan is dehydrated within the second reactor to produce isosorbide with the dehydrating being conducted at a temperature of at least 120° C.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In general, the invention pertains to method for processing sugars and for production of dianhydrosugars (also referred to as sugar alcohols). In conventional sugar dehydration a single-step reaction is typically performed utilizing a mineral acid catalyst, or in particular instances a solid acid catalyst, to produce a dehydration product. The dehydration product of conventional methodology typically contains a mixture of dianhydrosugar alcohols and can typically include one or more anhydrosugars. In contrast, methodology in accordance with the present invention can advantageously achieve greater selectivity of a particular dianhydrosugar product. More specifically, methodology of the invention utilizes a two-stage processing which can enhance selectivity of desirable intermediates, minimize undesired monoanhydrosugar intermediate formation and thereby increase selective production of the dianhydrosugar product.

Methodology in accordance with the invention can typically involve conducting a first-stage of sugar processing in a first reactor and conducting a second-stage of the overall processing in a second reactor. In order to conduct a first-stage of processing in accordance with the invention, an initial feed stream or starting material can be fed into a reactor. Although the first reactor can be a batch reactor, in particular instances it is preferable that the first reactor be a continuous reactor and that the starting material is passed through the continuous reactor.

The starting material is not limited to a particular form and can comprise one or more initial compounds in the presence or absence of a solvent. The initial starting material can include for example, a single sugar, or one or more sugars and/or anhydrosugars.

In the first reaction stage, one or more catalyst is provided within the first reactor and at least a portion of the initial compound(s) is converted to a monoanhydrosugar isomer. The conversion is conducted at a temperature of from about 70° C. to about 140° C., and preferably from about 90° C. to about 120° C. The monoanhydrosugar isomer is preferably an isomer capable of undergoing further dehydration to produce a particular desired dianhydrosugar product upon further dehydration processing (discussed below). Preferably, the first phase of the reaction is conducted at a temperature of less than about 120° C. For particular starting sugars such as for example, sorbitol, performing the first stage of the reaction at a relatively low temperature (less than 120° C.) can favorably affect the particular monoanhydrosugar isomer(s) formed during the first stage of processing. Such low temperature processing is preferably conducted in the presence of an acid catalyst within the reactor.

The low temperature acid catalyzed processing of a starting material comprising sorbitol can increase selective production of the 1,4-sorbitan monoanhydrosugar isomer relative to alternative isomers and can minimize production of 2,5-sugars (2,5-mannitan and 2,5-iditan). Since the undesirable 2,5-sugars are unable to be further dehydrated to produce isosorbide, the low temperature acid catalyzed processing in accordance with stage one of the invention can be especially useful where the ultimate desired product is the dianhydrosugar isosorbide, since the decreased 2,5-sugar production can enhance isosorbide yield.

As indicated above, sugars can be provided into the first reactor in an absence of solvent or can alternatively be provided in a mixture or solution. Where the starting material is an aqueous mixture, water can preferably be provided in the mixture to a final water content of less than or equal to about 70%, and typically to a content of from about 30% to about 70%.

Although not limited to a particular residence time within the first reactor, it can be preferable that the residence time be relatively short as compared to typical conventional methodology. The particular residence time may vary depending upon factors such as the particular starting material, the desired monoanhydrosugar intermediate(s) the catalyst utilized and the particular reactor type and size. Typically, and especially for starting materials containing sorbitol, residence within the first reactor in accordance with the invention is from about 10 minutes to about 30 minutes. The short residence time can minimize formation of undesirable intermediates (such as 2,5-sugars) for enhanced selectivity of intermediate production rather than maximization of conversion of the initial compounds. Any unconverted initial compounds can be recycled. Accordingly, the methodology of the invention can be more cost effective than conventional methodology.

In particular instances where sorbitol is utilized as an initial compound, processing in accordance with the invention within the first reactor selectively produces 1,4-sorbitan or 3,6-sorbitan relative to other monoanhydrosugars such as 2,5-iditan, and 2,5-mannitan. Methodology of the invention can advantageously reduce isomerization formation of 2,5-sugars or other undesirable monoanhydrosugars due to low temperature, short residence time and continuous removal of product which minimizes or avoids back-mixing Although not limited to a particular catalyst, the first stage of processing in accordance with the invention can preferably utilized an acid catalyst such as solid acid catalyst, a mineral acid catalyst, or a combination of mineral and/or solid acid catalysts. Exemplary solid acid catalysts which can be utilized individually or in combination with other solid acid catalysts and/or one or more mineral acid catalysts include but are not limited to a heteropolyacid, and an ion exchange resin, acidic clay, molecular sieve type material, sulfated zirconia, and mixtures thereof. Exemplary mineral acid catalysts which can be utilized individually or in combination with other mineral acid catalysts and/or solid acid catalysts include but are not limited to sulfuric acid, phosphoric acid, hydrochloric acid, p-toluenesulfonic acid, organic acid and mixtures thereof.

After stage one of the processing in accordance with the invention, the monoanhydrosugar isomer produced in the first stage is provided to a second reactor. The second reactor can be either a continuous reactor or a batch reactor.

Product material obtained from the first stage can be processed to separate a particular sugar isomer from so me or all of additional components of the product material or alternatively the desired isomer can be provided to the second reactor in the presence of such additional components. It can be advantageous to remove all or a portion of any undesirable monoanhydrosugar produced during stage one prior to providing the desired monoanhydrosugar to the second reactor to enhance selective production of dianhydrosugar product.

The second stage of the reaction is typically conducted under conditions which are relatively harsh as compared to stage one. For example, the temperature of stage two of the reaction is preferably greater than or equal to 120° C. In particular instances, reaction stage two can be conducted at a temperature of 130° C. or more. The increased temperature in stage two of the reaction can allow a short second reactor residence time. Preferably the residence time within the second reactor is less than or equal to about 30 minutes. A catalyst can optionally be provided during the second stage of the reaction and can comprise, for example, any of the catalysts discussed above with respect to reaction stage one. However, if the catalyst provided during stage two comprises a soluble acid catalyst, the concentration of such catalyst can optionally be decreased relative to the concentration utilized during stage one. The relatively high temperature and short residence time within the second reactor can advantageously enhance conversion of 1,4-sorbitan to isosorbide. The second reactor can be a batch reactor or can be a continuous reactor.

The overall two-stage processing in accordance with the invention, can allow high selectivity of monoanhydrosugar formation which can advantageously enhance overall selective dianhydrosugar production. Additionally, due to the increase in temperature upon entry of stage two of the reaction, overall production time can be short, allowing efficient dianhydrosugar formation.

Examples

Two-stage reaction processing in accordance with the invention was utilized to produce isosorbide. A 70% sorbitol starting material with a 30% volume of water was fed into a continuous reactor. One percent $H_2SO_4$ was utilized as a catalyst within the continuous reactor. Three independent reactions were conducted to compare monoanhydrosugar selectivity as a function of temperature and residence time. The results of the three exemplary stage one reactions are presented in Table 1.

TABLE 1

Conversion reaction first stage (continuous production): Conditions and Analysis

|  | Reaction 1 | Reaction 2 | Reaction 3 |
|---|---|---|---|
| Operating conditions |  |  |  |
| Catalyst | 1% $H_2SO_4$ | 1% $H_2SO_4$ | 1% $H_2SO_4$ |
| Vacuum | 8 mmHg | 8 mmHg | 8 mmHg |
| Temp (° C., at inlet) | 122 | 110 | 105 |
| Residence Time (hrs) | 2 | 2.5 | 2 |
| HPLC Data |  |  |  |
| Sorbitol | 8.22 | 16.95 | 61.42 |
| 2,5-sugars | 10.15 | 8.13 | 3.07 |
| 1,4-sorbitan | 37.92 | 68.60 | 28.17 |
| Isosorbide | 20.17 | 8.42 | 0.98 |
| Total | 76.5 | 102.0 | 93.6 |
| Performance |  |  |  |
| Conversion | 91.78 | 83.05 | 38.58 |
| 2,5-sugar selectivity | 14.9 | 9.55 | 9.52 |
| 1,4-sorbitan selectivity | 55.6 | 80.56 | 87.43 |
| Isosorbide selectivity | 29.5 | 9.89 | 3.0 |

To perform stage two of reaction processing in accordance with the invention, product from a single independent stage-one reaction was obtained from the continuous reactor and utilized as feed for three batch reactions independently in a second reactor. The feed composition comprised 68.98 wt % sorbitol; 15.59 wt % 1,4-sorbitan; 2.82 wt % isosorbide; and 2.3 wt % 2,5-sugars. The results of the stage-two study are presented in Table II. The "carbon balance" reported in Table II reflects a measurement based upon moles of carbon out versus moles of carbon into the reactor.

TABLE II

Conversion reaction stage 2: Conditions and analysis

|  | Reaction A | Reaction B | Reaction C |
| --- | --- | --- | --- |
| Reaction conditions (temp & time) | 130° C.; 30 min | 130° C.; 15 min | 120° C.; 30 min |
| Carbon Balance (out/in) | 100.9 | 92.3 | 91.3 |
| Conversion (%) | 97.6 | 93.3 | 95.8 |
| Yields (mol/mol) |  |  |  |
| Isosorbide | 83.2 | 39.5 | 71.1 |
| 1,4-sorbitan | 3.3 | 35.9 | 4.6 |
| 2,5 sugars | 12.4 | 10.6 | 11.4 |

At 100° C. for a reaction conducted over a time span of 30 minutes, conversion of 97.6% was observed with an isosorbide yield of 83.2%. Production of 2,5-sugars was observed to be very low.

The results of the studies above indicate that the two-stage processing in accordance with the invention can advantageously selectively produce 1,4-sorbitan in stage one of the reaction and thereby increase the overall reaction yield and selectivity of isosorbide.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method for production of a dianhydrosugar alcohol, comprising:
   providing a solid acid catalyst within a continuous reactor, the solid acid catalyst being selected from the group consisting of heteropolyacid and an ion exchange resin, acidic clay, molecular sieve material, and sulfated zirconia;
   passing a feed stream through the continuous reactor at a first temperature of from about 70° C. to about 120° C., the feed stream comprising at least one sugar and/or sugar alcohol in an absence of solvent upon entry into the reactor, at least a portion of the at least one sugar and/or sugar alcohol being converted to a monoanhydrosugar isomer during the passing, the residence within the continuous reactor being from about 10 minutes to about 30 minutes;
   obtaining a product material from the continuous reactor, the product material comprising the monoanhydrosugar isomer at an abundance of at least 50% relative to a total of monoanhydrosugars in the product material;
   separating the monoanhydrosugar isomer from undesirable monoanhydrosugars present in the product material; and
   after the separating, subjecting the monoanhydrosugar isomer to a second temperature to convert at least some of the monoanhydrosugar isomer to a dianhydrosugar alcohol, the second temperature being greater than the first temperature.

2. The method of claim 1 wherein the subjecting comprises providing the monoanhydrosugar isomer to a second reactor and dehydrating the monoanhydrosugar isomer to the dianhydrosugar alcohol.

3. The method of claim 2 wherein the second temperature is equal to or greater than 120° C.

4. The method of claim 2 wherein the dehydrating converts at least 90% of the monoanhydrosugar Isomer to a single dianhydrosugar alcohol.

5. The method of claim 1 wherein the initial compound is sorbitol.

6. The method of claim 1 wherein the monoanhydrosugar isomer is 1,4-sorbitan.

7. A method of producing isosorbide comprising:
   feeding an initial feed stream into a continuous reactor, the initial feed stream comprising sorbitol;
   exposing the sorbitol to an acid catalyst selected from the group consisting of heteropolyacid and an ion exchange resin, acidic clay, molecular sieve material, sulfated zirconia, sulfuric acid, phosphoric acid, hydrochloric acid p-toluenesulfonic acid and organic acids, within the continuous reactor, the exposing being conducted at a temperature of less than 120° C., a residence time for the reactor being less than or equal to about 30 minutes;
   converting at least some of the sorbitol to 1,4-sorbitan during the exposing;
   removing at least a portion of any 2,5-monoanhydrosugar produced during the exposing;
   after the removing, providing the 1,4-sorbitan in a second feed stream to a second reactor; and
   dehydrating at least some of the 1,4-sorbitan to produce isosorbide within the second reactor, the dehydrating being conducted at a temperature of at least 120° C.

8. The method of claim 7 wherein the dehydrating converts at least 83% of the 1,4-sorbitan to isosorbide.

9. The method of claim 7 wherein the acid catalyst comprises a mineral acid catalyst.

10. The method of claim 7 wherein the acid catalyst comprises a solid acid catalyst.

11. The method of claim 7 wherein the initial feed stream comprises from about 30% to about 70% water.

12. The method of claim 7 wherein the initial feed stream provides sorbitol in an absence of water.

13. A method for production of a dianhydrosugar alcohol, comprising:
   providing an acid catalyst within a first continuous reactor, the acid catalyst being selected from the group consisting of heteropolyacid and an ion exchange resin, acidic clay, molecular sieve material, sulfated zirconia, sulfuric acid, phosphoric acid, hydrochloric acid p-toluenesulfonic acid and organic acids;
   passing a feed stream comprising water and at least one of a sugar and a monoanhydrosugar through the first continuous reactor and subjecting the feed stream to a temperature of from about 70° C. to about 120° C. in the first continuous reactor for a residence time of from 10 minutes to 30 minutes;
   obtaining a product material from the first continuous reactor, the product material comprising a predominant monoanhydrosugar isomer and one or more additional monoanhydrosugar isomers;
   separating the predominant monoanhydrosugar isomer from the additional monoanhydrosugar isomers; and
   after the separating, in a second reactor, subjecting the predominant monoanhydrosugar isomer to a temperature of at least 120° C. to produce a dianhydrosugar alcohol.

14. The method of claim 13 wherein the second reactor contains an acid catalyst selected from the group consisting of heteropolyacid and an ion exchange resin, acidic clay, molecular sieve material, sulfated zirconia, sulfuric acid, phosphoric acid, hydrochloric acid p-toluenesulfonic acid and organic acids.

15. The method of claim 13 wherein the feed stream contains from 30% to about 70% water.

16. The method of claim 13 wherein a residence time in the second reactor is less than or equal to 30 minutes.

17. The method of claim 13 wherein the second reactor is a batch reactor.

18. The method of claim 13 wherein the second reactor is a continuous reactor.

* * * * *

UNITED STATES PATENT AND TRADEMARK OFFICE
CERTIFICATE OF CORRECTION

PATENT NO. : 7,615,652 B2 Page 1 of 1
APPLICATION NO. : 11/341930
DATED : November 10, 2009
INVENTOR(S) : Holladay et al.

It is certified that error appears in the above-identified patent and that said Letters Patent is hereby corrected as shown below:

Title Page, should read (*) Notice: Subject to any disclaimers, term of this patent is extended or adjusted under 35 U.S.C. 154(b) by 591 days.

Col. 3, Line 36 – Insert --.-- after "back-mixing".

Col. 3, Line 39 – Replace "utilized" with --utilizes--.

Col. 3, Line 57 – Replace "so me" with --some--.

Col. 6, Line 8 Claim 4 – Replace "Isomer" with --isomer--.

Signed and Sealed this

Third Day of August, 2010

David J. Kappos
*Director of the United States Patent and Trademark Office*